(12) United States Patent
Krauss et al.

(10) Patent No.: US 7,045,634 B2
(45) Date of Patent: May 16, 2006

(54) PROSTAMIDE RECEPTOR ANTAGONISTS

(75) Inventors: Achim H. Krauss, San Marcos, CA (US); David F. Woodward, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 32 days.

(21) Appl. No.: 10/893,054

(22) Filed: Jul. 16, 2004

(65) Prior Publication Data
US 2005/0054699 A1    Mar. 10, 2005

Related U.S. Application Data

(60) Provisional application No. 60/500,566, filed on Sep. 5, 2003.

(51) Int. Cl.
*C07D 236/32* (2006.01)
(52) U.S. Cl. .................................. 548/236
(58) Field of Classification Search ............ 548/236
See application file for complete search history.

(56) References Cited

U.S. PATENT DOCUMENTS

| | | | |
|---|---|---|---|
| 4,632,928 A | 12/1986 | Rettegi et al. | |
| 5,100,889 A | 3/1992 | Misra et al. | |
| 5,153,327 A * | 10/1992 | Misra et al. | 548/237 |
| 5,605,917 A * | 2/1997 | Ogletree | 514/365 |
| 5,747,660 A | 5/1998 | Orlicky | |
| 5,955,575 A | 9/1999 | Peri et al. | |
| 6,369,089 B1 | 4/2002 | Burk et al. | |
| 6,395,787 B1 | 5/2002 | Woodward et al. | |
| 6,407,250 B1 * | 6/2002 | Burk et al. | 548/112 |
| 6,509,364 B1 * | 1/2003 | Burk et al. | 514/374 |
| 6,511,999 B1 | 1/2003 | Burk et al. | |
| 2002/0094974 A1 * | 7/2002 | Castelhano et al. | 514/210.21 |
| 2002/0165399 A1 * | 11/2002 | Burk et al. | 548/117 |

FOREIGN PATENT DOCUMENTS

| | | | |
|---|---|---|---|
| EP | 0391652 A1 * | 2/1990 | |
| EP | 0391652 | 10/1990 | |
| EP | 391652 A1 * | 10/1990 | |
| EP | 0448274 A2 | 9/1991 | |
| EP | WO 02/22620 | 3/2002 | |

OTHER PUBLICATIONS

Albuquerque, et al. "Four-Dimensional Quantitative Structure-Activity Relationship Analysis of a Series of Interphenylene 7-Oxabicycloheptane Oxazole Thromboxane A2 Receptor Antagonists," J. Chem. Inf. Comput. Sci., vol. 38, pp. 925-938 (1998).*

Misra, et al. "Interphenylene 7-Oxabicyclo[2.2.1]heptane Oxazoles. Highly Potent, Selective, and Long-Acting Thromboxane A2 Receptor Antagonists," J. Med.Chem. vol. 36, pp. 1401-1417 (1993).*

Misra et al., "Interphenylene 7-oxabicyclo[2.2.1]heptane oxazoles. Highly potent, selective, and long-acting thromboxane A2 receptor antagonists," J. Med. Chem., vol. 36, No. 10, pp. 1401-1417 (1993).*

Liang et al, "Composition of Prostaglandin F2a, Bimatoprost (Prostamide), and Butaprost (EP2 Agonist) on Cyr61 and Connective Tissue Growth Factor Gene Expression", Journal of Biological Chemistry, vol. 278, No. 29, Jul. 18, 2003, pp. 27267-27277.

Koda et al, "Synthesis of prostaglandin F ethanolamide by prostaglandin F synthase and identification of Bimatoprost as a potent inhibitor of the enzyme: new enzyme assay method using LC/ESI/MS", Archives of Biochemistry and Biophysics, vol. 424, No. 2, Apr. 15, 2004, pp. 128-136.

Gandolfi et al, "Effect of Bimatoprost on Patients with Primary Open-angle Glaucoma or Ocular Hypertension Who are Nonresponders to Latanoprost", Ophthalmology, vol. 110, No. 3, Mar. 2003, 609-614.

Misra et al, "Interphenylene 7-Oxabicyclo [2.2.1]heptane Oxazoles. Highly Potent, Selective, and Long-Acting Thromboxane $A_2$ Receptor Antagonists", J. Med. Chem., 1993, 36, 1401-1417.

* cited by examiner

*Primary Examiner*—Kamal A. Saeed
*Assistant Examiner*—Nyeemah Grazier
(74) *Attorney, Agent, or Firm*—Robert J. Baran; Brent A. Johnson; Martin A. Voet

(57) ABSTRACT

The present invention provides prostamide receptor antagonist compounds that may be represented by the general formula I.

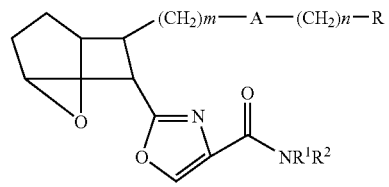

wherein A, $R^1$, $R^2$, $R^3$, $R^4$ and $R^6$ are as defined in the specification.

1 Claim, 5 Drawing Sheets

Effect of Example 1 on Prostamide $F_{2\alpha}$ Induced Cat Iris Contraction

Effect of Example 1 on $PGF_{2\alpha}$ Induced Cat Iris Contraction

PROSTAMIDE RECEPTOR ANTAGONISTS

This patent application claims benefit of priority under 35 USC § 119(e) to provisional patent application 60/500,566, filed Sep. 5, 2003, which is hereby incorporated by reference herein.

BACKGROUND OF THE INVENTION

1. Field of the Invention

The present invention provides prostamide receptor antagonists, e.g. prostamide $F_{2\alpha}$ receptor antagonists.

2. Description of Related Art

Prostamides are disclosed in U.S. Pat. No. 6,395,787, hereby incorporated by reference in its entirety, as useful to lower elevated intraocular pressure and for treating glaucoma. These compounds are structurally related to prostaglandins, e.g. Prostaglandin $F_{2\alpha}$, which are also useful in lowering elevated intraocular pressure, but prostamides do not act through the FP receptor to lower intraocular pressure. As such, prostamides do not have the same effects as prostaglandins when utilized to treat elevated intraocular pressure and/or glaucoma. For example, it has been demonstrated that bimatoprost, a synthetic analog of prostamide $F_{2\alpha}$, lowers intraocular pressure in patients unresponsive to the synthetic prostaglandin $F_{2\alpha}$ analog latanoprost (Gandolfi and Cimino, Ophthalmology 110:609, 2003).

It would be desirable to have prostamide receptor antagonists to assist in pharmacologically defining prostamide receptors to aid in determining compounds which have activity at the prostamide receptor. Heretofore, compounds having prostamide receptor antagonist activity have been unknown.

Prostaglandin $F_{2\alpha}$ antagonists are reported in U.S. Pat. Nos. 4,632,928; 5,747,660; and 5,955,575. The $PGF_{2\alpha}$ antagonists of U.S. Pat. No. 4,632,928 are pyrazole derivatives having an ergoline skeleton. The $PGF_{2\alpha}$ antagonist of U.S. Pat. No. 5,747,660 is a prostaglandin $F_{2\alpha}$ receptor regulatory protein (FPRP) which is able to inhibit the binding of $PGF_{2\alpha}$ to its receptor.

Novel prostaglandin $F_{2\alpha}$ antagonists are reported in U.S. Pat. Nos. 6,369,089; 6,407,250; 6,509,364 and 6,511,999 which are hereby incorporated by reference in their entirety.

Interphenylene 7-Oxabicyclo [2.2.1] heptane oxazoles, useful as Thromboxane $A_2$ receptor antagonists are reported in U.S. Pat. Nos. 5,100,889 and 5,153,327, European Patent Application 0 391 652 and J. Med. Chem. 1993, 36, 1401–1417.

Thromboxane $A_2$ receptor antagonists, e.g. 7-oxabicycloheptyl substituted heterocyclic amide prostaglandin analogs, alone, or in combination with anti-inflammatory agents are useful in treating ulcerative gastrointestinal conditions and dysmenorrhea as disclosed in European Patent Application 0 448 274 and U.S. Pat. No. 5,605,917.

BRIEF SUMMARY OF THE INVENTION

The invention relates to prostamide receptor antagonists, e.g. prostamide $F_{2\alpha}$ receptor antagonists and their use in determining compounds having activity at the prostamide receptor, i.e. prostamide receptor agonists.

The compounds useful as prostamide receptor antagonists of the present invention may be represented by the general formula I.

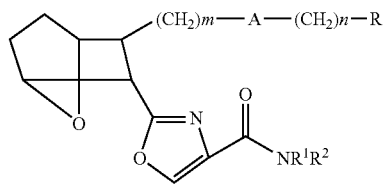

wherein m is an integer of from 1 to 3, preferably 1 or 2;

n is 0 or an integer of from 1 to 4, preferably from 2 to 4;

A is an aryl or heteroaryl radical having from 6 to 14 carbon atoms, wherein said heteroaryl may be substituted with one or more oxygen, sulfur or nitrogen in the heteroaryl ring and heteroatom substituted derivatives thereof;

R is $CONR^3R^4$;

$R^1$ and $R^2$ are independently selected from the group consisting of H, $C_1$–$C_6$ alkyl, $C_2$–$C_6$ alkenyl, $C_2$–$C_6$ alkynyl, $C_3$–$C_7$ cycloalkyl, $C_4$–$C_{12}$ alkylcycloalkyl, $C_6$–$C_{10}$ aryl, $C_7$–$C_{12}$ alkylaryl radicals and heteroatom-substituted derivatives thereof, wherein one or more of the hydrogen or carbon atoms in said radicals may be replaced with a halogen, oxygen, nitrogen or sulfur-containing radical;

$R^3$ and $R^4$ are independently selected from the group consisting of H, $C_1$–$C_6$ alkyl, $C_2$–$C_6$ alkenyl, $C_2$–$C_6$ alkynyl, $C_3$–$C_7$ cycloalkyl, $C_4$–$C_{12}$ alkylcycloalkyl, $C_6$–$C_{10}$ aryl, $C_7$–$C_{12}$ alkylaryl radicals and heteroatom-substituted derivatives thereof, wherein one or more of the hydrogen or carbon atoms in said radicals may be replaced with a halogen, oxygen, nitrogen or sulfur-containing radical; and pharmaceutically acceptable salts thereof.

The preferred substituents for $R^1$, $R^2$, $R^3$ and $R^4$ are selected from the group consisting of hydroxyl, halogen, e.g. fluoro or chloro, $COOR^6$, $NO_2$, $N(R^6)_2$, $SR^6$, sulfoxy, sulfone, CN and $OR^6$.

These compounds are especially useful for determining compounds having prostamide agonist activity, e.g. prostamide $F_{2\alpha}$ activity, as well as for treating a number of diseases. For instance, prostamide antagonists may be useful in treating hyperpigmentary disorders of the skin, hair, internal organs or other pigmented cells. Additionally, prostamide antagonists may be useful in reducing hair growth, e.g. in case of hirsutism or in instances where a reduction or prevention of hair growth may be desirable. Also, prostamide agonists may be useful in treating ocular hypotony associated with disease or surgery.

DETAILED DESCRIPTION OF THE INVENTION

In the prostamide receptor antagonists of the present invention, A may be represented by the general formula

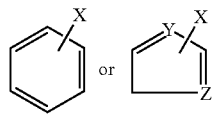

wherein X is selected from the group consisting of H, $R^6$, hydroxy, halogen, e.g. fluoro or chloro, $COOR^6$, $NO_2$, $CF_3$, $N(R^6)_2$, $CON(R^6)_2$, $SR^6$, sulfoxy, sulfone, CN and $OR^6$ wherein $R^6$ is $C_1$–$C_6$ alkyl; Y is O or S; Z is N or CH Preferably, the prostamide antagonist compounds are represented by the general formula II.

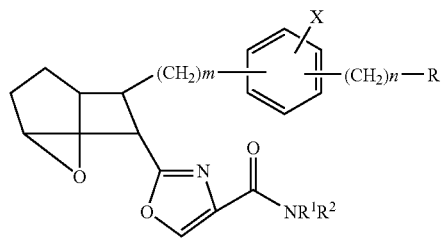

or general formula III

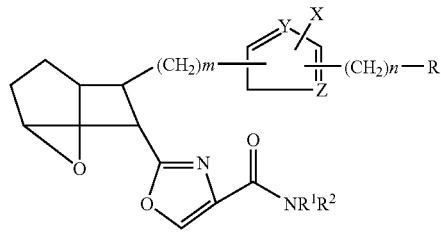

Preferably, $R^1$ and $R^2$ are selected from the group consisting of H, $C_1$–$C_6$ alkyl, $C_3$–$C_7$ cycloalkyl and $C_4$–$C_{12}$ alkylcycloalkyl.

Preferably $R^3$ and $R^4$ are selected from the group consisting of H, $C_1$–$C_6$ alkyl and hydroxyl derivatives thereof.

Preferably X is selected from the group consisting of hydrogen or halogen, e.g. fluoro.

Figure 5:
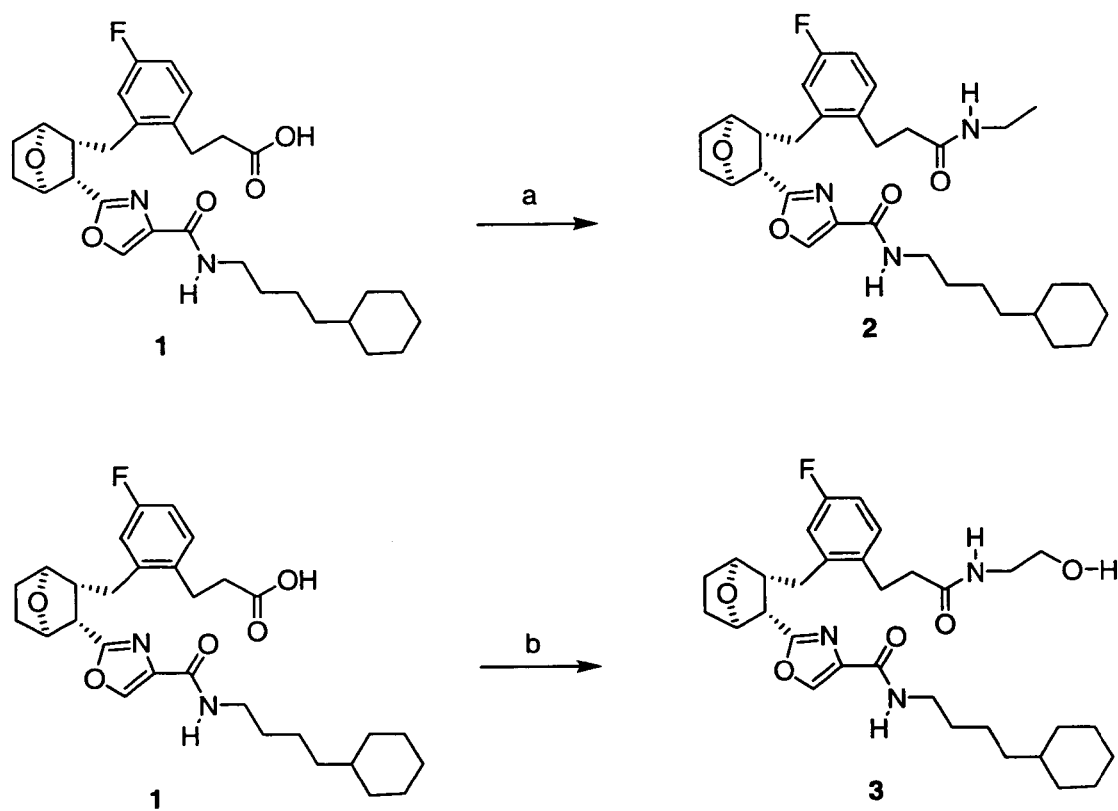
FIG. 5 shows the synthetic schemes for the preparation of the prostamide antagonists of Examples 1 and 2.

The following Examples describe a method of synthesizing the prostamide antagonist compounds of the invention wherein the numbering of the Examples corresponds to the numbering of the various intermediates and final compounds shown in FIG. 5.

EXAMPLE 1

2-{3-[2-(2-Ethylcarbamoyl-ethyl)-5-fluoro-benzyl]-7-oxa-bicyclo[2.2.1]hept-2-yl}-oxazole-4-carboxylic acid (4-cyclohexyl-butyl)-amide (2)

DMF (0.22 mL) and ethyl amine (77 µL, 0.15 mmol) were added to 3-(2-{(1S,2R,3S)-3-[4-(4-Cyclohexyl-butylcarbamoyl)-oxazol-2yl]-7-oxa-bicyclo[2.2.1]hept-2-ylmethyl}-4-fluoro-phenyl)-propionic acid (1) (28 mg, 0.053 mmol), EDCI [1-(3-dimehylaminopropyl)-3-ethylcarbodiimide hydrochloride] (17 mg, 0.089 mmol) and DMAP (8 mg, 0.065 mmol). The solution was stirred for 23 h and then was diluted with 15 mL ethyl acetate and washed with HCl (1 M, 3×15 mL). The ethyl acetate solution was then dried ($Na_2SO_4$), filtered and evaporated. Flash chromatography on silica gel (ethyl acetate) gave a mixture of the starting acid and the product amide. Purification by preparative thin layer chromatography (4% methanol/dichloromethane) gave the title amide (6 mg, 0.011 mmol, 20%). $^1H$ NMR (300 MHz, ppm) δ 8.06 (s, 1 H) 7.1–7.0 (m, 2 H) 6.8–6.7 (m, 2 H) 5.43 (br s, 1 H) 4.97 (d, J=4.4 Hz, 1 H) 4.82 (d, J=4.4 Hz, 1 H) 3.4–3.3 (m, 3 H) 3.3–3.2 (m, 2 H) 2.9–2.8 (m, 2 H) 2.6–2.5 (m, 1 H) 2.3–2.1 (m, 4 H) 1.8–0.8 (m, 24 H).

EXAMPLE 2

2-(3-{5-Fluoro-2-[2-(2-hydroxy-ethycarbamoyl)-ethyl]-benzyl}-7-oxa-bicyclo[2.2.1]hept-2-yl)-oxazole-4-carboxylic acid (4-cyclohexyl-butyl)-amide (3)

A dichloroethane (0.3 mL) solution of 3-(2-{(1S,2R,3S)-3-[4-(4-Cyclohexyl-butylcarbamoy)-oxazol-2-yl]-7-oxa-bicyclo[2.2.1]hept-2-ylmethyl}-4fluoro-phenyl)-propionic acid (1) (30 mg, 0.057 mmol) was treated with triethylamine (12 µL, 0.086 mmol) and ethyl chloroformate (7 µL, 0.073 mmol). After 30 min., ethanolamine (10 µL, 0.17 mmol) was added and the solution stirred for 18 h. The resulting mixture was partitioned between 10 mL 1 M NaOH and 15 mL dichloromethane. The dichloromethane solution was washed with 1 M NaOH (6×10 mL). A small amount of brine was added to avoid an emulsion. The dichloromethane solution was then washed with brine (15 mL) and then was dried ($Na_2SO_4$), filtered and evaporated. Purification by preparative thin layer chromatography (4% methanol/dichloromethane) gave 12 mg (0.021 mmol, 37%) of the title compound. $^1H$ NMR (300 MHz, ppm) δ 8.11 (s, 1 H) 7.3–7.2 (m, 1 H) 7.11–7.06 (m, 1 H) 6.84–6.78 (m, 2 H) 6.2–6.1 (m, 1 H) 5.00 (d, J=4.0 Hz, 1 H) 4.81 (d, J=4.4 Hz, 1 H) 3.7–3.6 (br m, 2 H) 3.5–3.3 (m, 6 H) 2.84–2.79 (m, 2 H) 2.66–2.57 (m, 1 H) 2.4–2.0 (m, 4 H) 1.9–0.8 (overlapping m, 21 H).

The compounds of Examples 1 and 2 were tested for prostamide antagonist activity as follows:

The smooth muscle tension of isolated tissue preparations was measured isometrically with force displacement transducers (Grass FT-03) and recorded on a Grass polygraph (Model 7G). The organ baths contained Krebs solution maintained at 37° C. and gassed with 95% $O_2$: 5% $CO_2$ to give a pH of 7.4. The Krebs solution had the following composition (mM): NaCl, 118.0; KCl, 4.7; $KH_2PO_4$, 1.2; $CaCl_2$, 1.9; $MgSO_4$, 1.18; $NaHCO_3$, 25.0; glucose, 11.7; indomethacin, 0.001.

Cat Iris Sphincter

Adult domestic cats were sacrificed by intravenous overdose of sodium pentobarbitol (Anthony, Arcadia, Calif., USA). The eyes were enucleated immediately and placed on ice. The iris sphincter from each eye was dissected to provide two strips ~3 mm wide and 15–20 mm long. The sphincter muscle was mounted vertically under 50 mg tension in a jacketed 10 ml organ bath. A 60 min. equilibration period was allowed before commencing each experiment. The response to $1×10^{-7}$ M $PGF_{2α}$ was determined at the beginning of each experiment as a reference. After complete washout, and return to baseline tension, tissues were allowed to re-equilibrate for 30 min. Antagonist or vehicle were then added. After a 30 min incubation period test compounds were added cumulatively to the organ bath. Activity of test compounds was determined as contractile responses and expressed relative to the reference standard $1\times10^{-7}$ M $PGF_{2\alpha}$.

Figure 1:
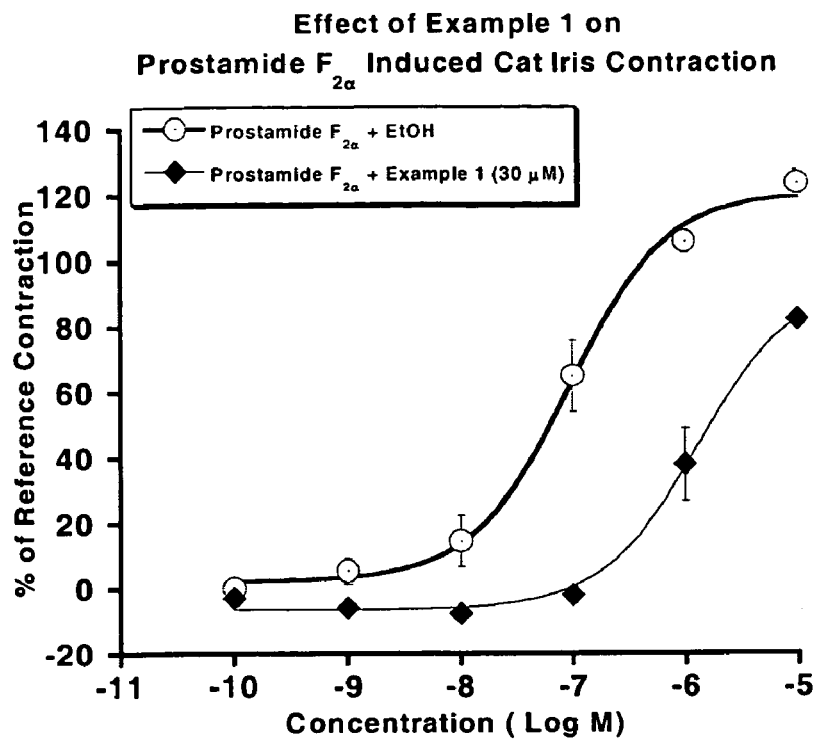
FIG. 1 shows the prostamide $F_{2\alpha}$ antagonist activity of the compound of Example 1.
Figure 1:
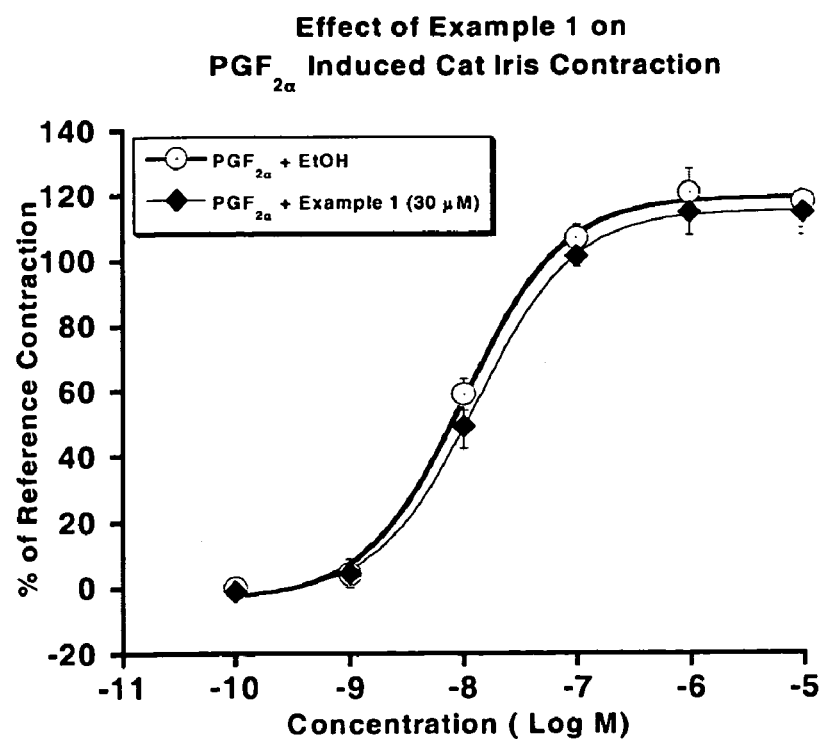
Figure 2:
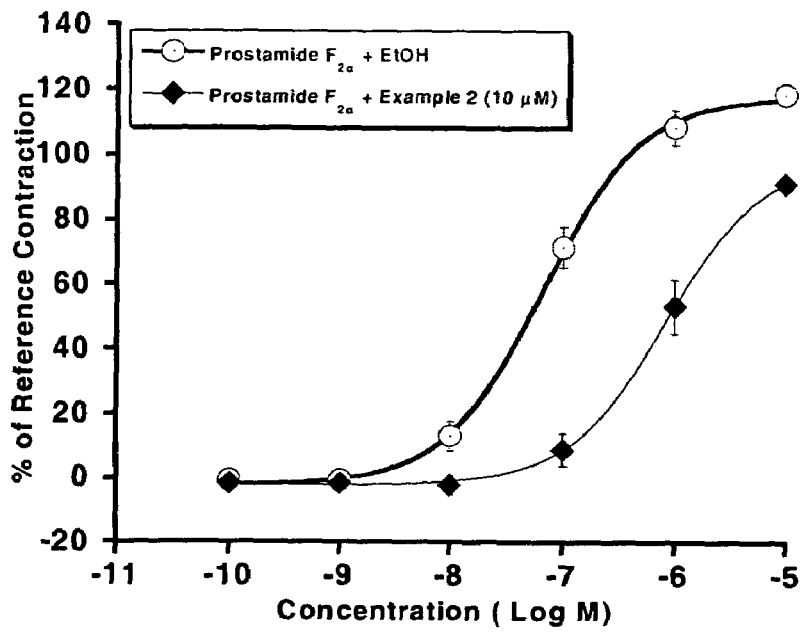
FIG. 2 shows the prostamide $F_{2\alpha}$ antagonist activity of the compound of Example 2.
Figure 2:
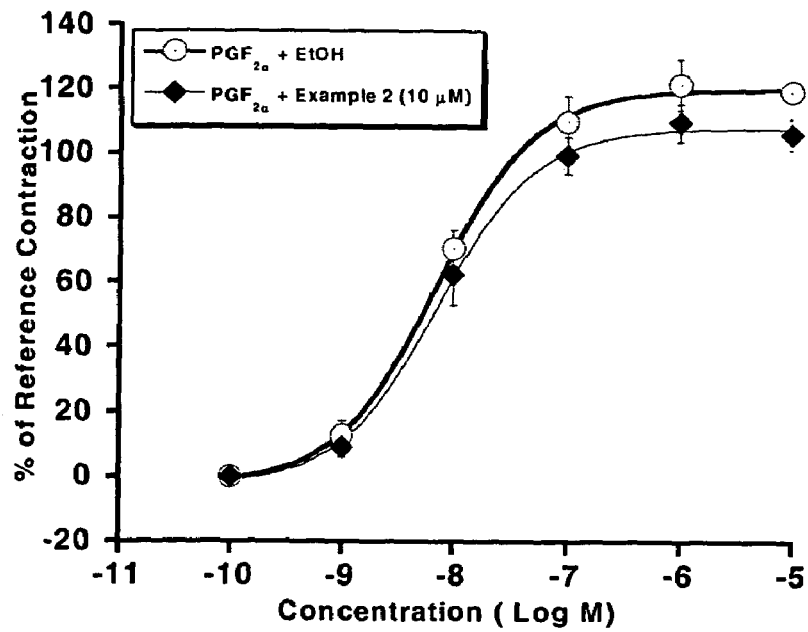

As shown in FIG. 1, the prostamide antagonist of Example 1 displaces the response curve of prostamide $F_{2\alpha}$, while it does not effect the response curve of $PGF_2\alpha$. Prostamide $F_{2\alpha}$ is the 1-ethanolamide of $PGF_{2\alpha}$ As shown in FIG. 2, the prostamide antagonist of Example 2 displaces the response curve of prostamide $F_{2\alpha}$, while it does not effect the response curve of $PGF_{2\alpha}$.

Figure 3:
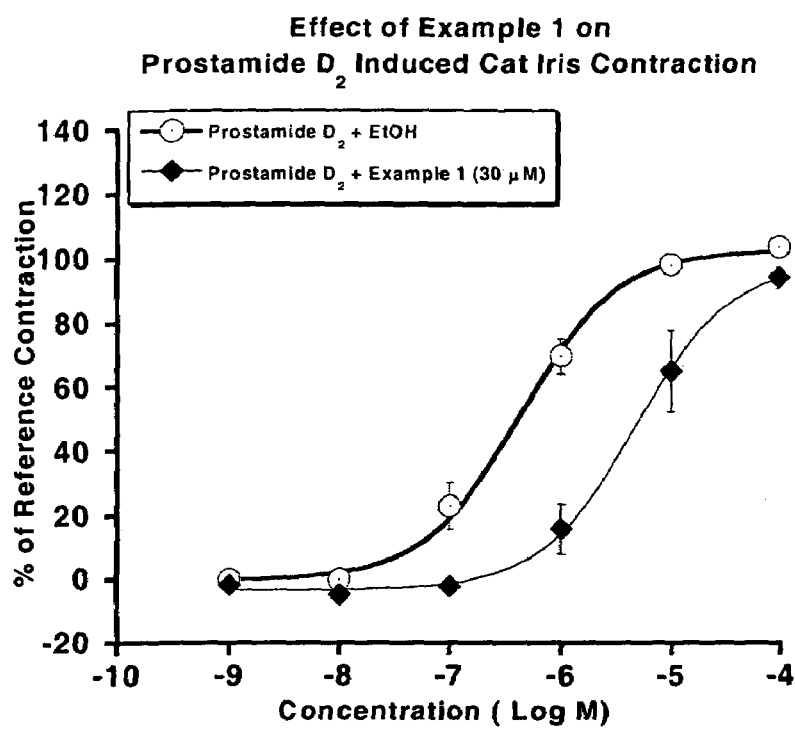
FIG. 3 shows the prostamide $D_2$ antagonist activity of the compound of Example 1.
Figure 3:
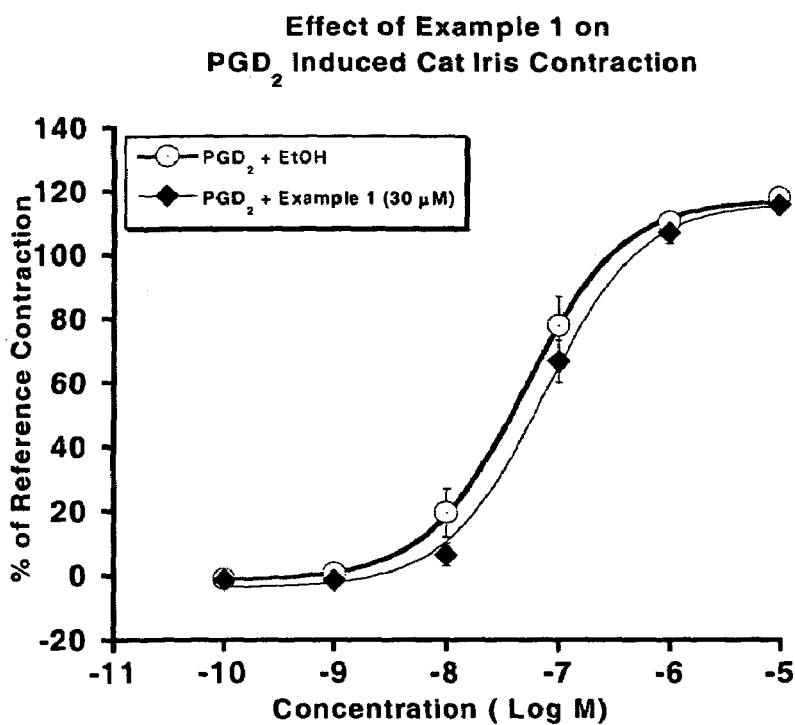

As shown in FIG. 3, the prostamide antagonist of Example 1 displaces the response curve of prostamide $D_2$, while it does not effect the response curve of $PGD_2$. Prostamide $D_2$ is the 1-ethanolamide of $PGD_2$.

Figure 4:
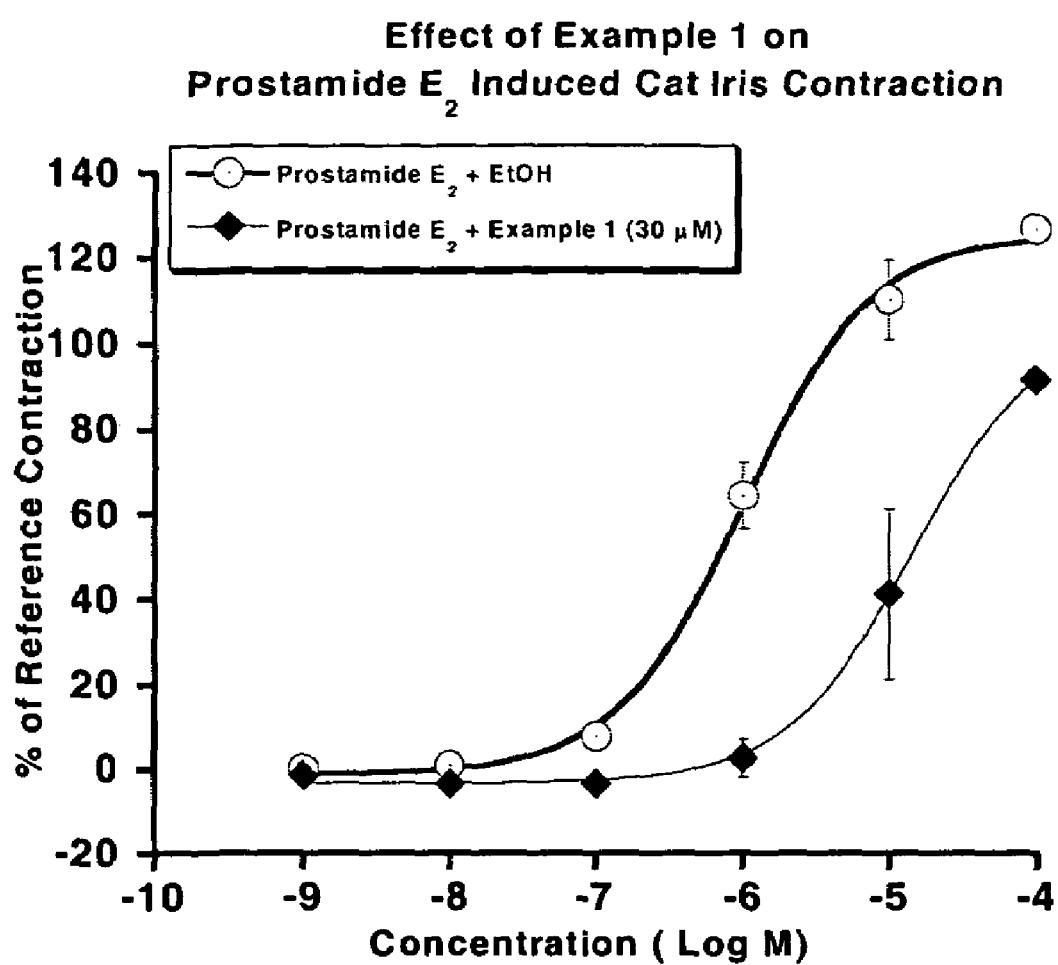
FIG. 4 shows the prostamide $E_2$ antagonist activity of the compound of Example 1.

As shown in FIG. 4, the prostamide antagonist of Example 1 displaces the response curve of prostamide $E_2$, while it does not effect the response curve of $PGE_2$. Prostamide $E_2$ is the 1-ethanolamide of $PGE_2$.

Thus, as shown in the Figures and associated working examples, the prostamide antagonists of the present invention may be used to test for compounds having prostamide receptor agonist activity and not activity at the corresponding prostaglandin receptor as follows:

A tissue or cell responsive to a prostaglandin and a prostamide, e.g. cat iris sphincter tissue, is contacted with various concentrations of said prostaglandin and a first response is measured in a concentration dependent manner. (Preferably, the cat iris sphincter tissue may be dissected into four paired preparations for the purpose of the following test.) Said tissue or cell is contacted with said various concentrations of said prostaglandin in the presence of a prostamide antagonist and a second response is measured in a concentration dependent manner.

Said tissue or cell is contacted with various concentrations of a compound which is to be evaluated for prostamide agonist activity and a third response is measured in a concentration dependent manner. Said tissue or cell is contacted with said various concentrations of said compound which is to be evaluated for prostamide agonist activity in the presence of said prostamide antagonist and a fourth response is measured in a concentration dependent manner.

Compounds having prostamide agonist activity are determined as compounds wherein the difference between said third and fourth response is greater than the difference between said first and second response.

Preferably, the difference between said first and second response is substantially negligible, i.e. the prostaglandin has substantially no prostamide agonist activity, therefore the presence of the prostamide antagonist does not affect the tissueresponse. Thus, prostamide agonists are compounds wherein the response in the presence of the prostamide antagonist is negliglible as compared to the response in the absence of the prostamide antagonist.

In another aspect of the present invention, the relative activity of a prostamide agonist may be measured by contacting two or more prostamide agonists with a tissue or cell that is responsive to a prostamide agonist in the presence of a specified concentration of a prostamide antagonist of this invention. The relative activity of each of said prostamide agonists is determined by, comparing the relative response of said tissue or cell.

The compounds of the invention can be administered orally, parenterally, or topically to various mammalian species known to be subject to hyperpigmentary disorders of the skin, hair, internal organs or other pigmented cells or excessive hair growth, e.g., humans, cats, dogs and the like in an effective amount within the dosage range of about 0.1 to about 100 mg/kg, preferably about 0.2 to about 50 mg/kg and more preferably about 0.5 to about 0.5 to about 25 mg/kg (or from about 1 to about 2500 mg; preferably from about 5 to about 2000 mg) on a regimen in single or 2 to 4 divided daily doses.

The active ingredient can be utilized in a composition such as tablet, capsule, solution or suspension containing about 5 to about 500 mg per unit of dosage of a compound or mixture of compounds of formulas I, II or III in topical form for reducing pigmentation or hair growth, etc. (0.01 to 5% by weight compound of formulas I, II or III, 1 to 5 treatments per day). They may be compounded in conventional matter with a physiologically acceptable vehicle or carrier, excipient, binder, preservative, stabilizer, flavor, etc., or with a topical carrier such as mineral oil as called for by accepted pharmaceutical practice.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds. Different pharmaceutical compositions, including the prostamide antagonists of this invention, may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. The compound which is 2-(3-{5-Fluoro-2-[2-(2-hydroxy-ethycarbamoyl)-ethyl]-benzyl}-7-oxa-bicyclo[2.2.1]hept-2-yl)-oxazole-4-carboxylic acid (4-cyclohexyl-butyl)-amide.

* * * * *